United States Patent [19]

Matsuno et al.

[11] Patent Number: 5,350,688
[45] Date of Patent: Sep. 27, 1994

[54] METHOD FOR REGENERATION OF RICE PLANTS

[75] Inventors: Tsukanori Matsuno; Keiichiro Ishizaki, both of Kitsuregawa, Japan

[73] Assignee: Kirin Beer Kabushiki Kaisha, Tokyo, Japan

[21] Appl. No.: 899,218

[22] Filed: Jun. 16, 1992

Related U.S. Application Data

[63] Continuation of Ser. No. 661,839, Feb. 27, 1991, abandoned, which is a continuation of Ser. No. 331,679, Mar. 30, 1989, abandoned.

[30] Foreign Application Priority Data

Mar. 31, 1988 [JP] Japan .................................. 63-80211

[51] Int. Cl.⁵ ............................................. A01H 4/00
[52] U.S. Cl. ............................ 435/240.5; 435/240.48; 800/DIG. 57
[58] Field of Search ........... 435/240.4, 240.48, 240.49, 435/240.5, 240.54; 800/DIG. 57

[56] References Cited

PUBLICATIONS

Pat. application Ser. No. 07/661,875 by Matsuno et al.
Kishor et al (1986) J. Plant Physiol. 126:49–54.
Wang et al (1987) Plant Cell Reports 6:294–296.
Abe et al (1986) Japan J. Breed. 36:1–6.
Kishor (1987) Plant Science 48:189–194.
Li Su Nam, et al (1986) Cereal Research Communications 14(2):197–203.
Aziz Miah et al (Jun. 1984) Bangladesh J. Bot 13(1):112–113.
Plant Tissue Culture: Theory and Practice, edited by S. S. Bhojwani and M. K. Razdan (1983) pp. 91–99.
Kishor et al., Ind. J. Exp. Biol. 24, 700–702 (1986).
Kishor et al., Plant Cell Rep., 5, 391–393 (1986).

*Primary Examiner*—Che S. Chereskin
*Attorney, Agent, or Firm*—Gray Cary Ware & Freidenrich

[57] ABSTRACT

A method is provided for inducing rice callus having embryogenic potency by culturing a rice explant in a liquid medium containing at least inorganic salts, a carbon source, one or more auxins and an osmotic regulator, and for proliferating the callus obtained by subculturing in a similar medium. This method enables the clonal proliferation of rice, so that the invention is useful for the industrial large-scale production of seedlings of all cultivars of rice including non-true bred cultivars and non-true bred lines.

4 Claims, 7 Drawing Sheets

METHOD FOR REGENERATION OF RICE PLANTS

RELATED APPLICATION DATA

This is a continuation of Ser. No. 661,839, filed Feb. 27, 1991, abandoned, which is a continuation of commonly owned and co-pending application Ser. No. 07/331,679, filed Mar. 30, 1989 now abandoned.

FIELD OF THE INVENTION

This invention relates to the large-scale proliferation of rice plants (*Oryza sativa* L.) using plant tissue culture techniques. More specifically, this invention relates to a method for inducing and proliferating rice callus having embryogenic potency.

BACKGROUND OF THE INVENTION

Recent advances in tissue culture techniques have established the potential for commercialization of large-scale proliferation for numerous plant species. For rice (*Oryza sativa* L.), techniques which suggest the possibility of large-scale proliferation have been reported. However, it is unclear whether they have attained a commercially applicable level of efficiency.

Two techniques have been proposed for proliferating rice by tissue culture. The first involves differentiating and inducing the formation of an adventitious bud or an somatic embryo directly from an explant tissue to proliferate rice plants. This technique has been reported (Ling, D. H. et al., *Plant Cell Reports* 2, 172 (1983); Wernicke, W. et al., *Z. Pflanzenphysiol.* 103, 361 (1981); *Eur. J. Cell Biol.* 24, 347 (1981); Stuart, D. A. and S. G. Strickland, WO 87/02701). In this technique, however, the differentiation and induction ratios reported for individuals or somatic embryos are very low. Thus, this technique appears impracticable from the standpoint of proliferation efficiency for large-scale proliferation on a commercial basis.

A second technique involves inducing and proliferating a callus culture from a rice explant tissue, then inducing and producing a somatic embryo or an adventitious bud from the callus tissue and finally regenerating the embryo or adventitious bud into a whole plant. Although many sites on a rice plant, such as ovary, anther, immature embryo, full-ripe seed, juvenile leaf, root, shoot apex, juvenile panicle, etc., can be used as explants for the induction of rice callus, the reported redifferentiation ratios are low. Thus, this technique has not been shown to be practical as a proliferation technique for obtaining a large number of regenerated individual plants from a small amount of explant material.

As pointed out by Nabors, W. M. and J. W. Heyser (*Plants* 157., 385 (1983)), Siriwardana, S. and M. W. Nabors (*Plant Physiol.* 73, 143 (1983)), and others, calli induced from explant material can be classified into two groups, that is, embryogenic callus having embryogenic potency (hereinafter referred to as "E callus") and nonembryogenic callus having no embryogenic potency (hereinafter referred to as "NE callus"). In many cases, both types of calli are present as a mixture in culture. It has been found that the individual regeneration potency of the overall callus culture is directly related to the proportion of E callus present. However, the proportion of NE callus in a culture generally increases with the passage of time and as proliferation progresses, and thus the individual regeneration potency tends to decrease. It is believed that this phenomenon is due to a higher proliferation rate for NE callus than E callus, and because E callus can convert to NE callus in culture, whereas NE callus will not convert to E callus.

In order to improve the redifferentiation ratio of rice tissue culture, it may be possible, e.g. to induce E calli from explants and serially transfer the E calli to allow proliferation without conversion to NE calli; to separate E calli from the induced calli; to invent a selective medium in which E calli alone can be proliferated; or the like. However, there are no known reports of practicable techniques based on these ideas.

In order to make large-scale proliferation a commercially applicable technique, it is necessary to induce and proliferate a suspension culture consisting of E calli alone. Generally, a suspension culture is obtained by placing an explant on an agar medium containing auxin, inducing a callus and then transferring the callus into a liquid medium. Examples of the culture of an explant performed in a liquid medium from the beginning of culture include the reports by Zimny and Lörz (*Plant Cell Reports* 5, 89 (1986)) and Toriyama and Hinata (*J. Breed.* 36, suppl. 2, 50 (1986)) among others. However, in these examples, NE calli constituted the majority of the suspensions obtained. The redifferentiation ratio obtained by Toriyama and Hinata (1986) was as low as 2% per callus.

P. B. Kavikishor (*Plant Science* 48, 189 (1987)) suggested that the addition of an osmotic regulator to an agar medium is effective for the proliferation of callus and the redifferentiation of foliage. In this report, however, the redifferentiation ratio stayed at a low frequency of 1 individual plant per 300 mg of callus. Stuart and Strickland (supra, (1987)) suggested that the addition of various amino acids, particularly L-proline, was effective for the formation of somatic embryos from callus. In addition, other reports have suggested that casein hydrolysate, yeast extract, etc., are effective substances for increasing redifferentiation efficiency (Abe and Futsuhara [*Japan J. Breed.* 34, 147 (1984); *Japan Physiol.* 121, 111 (1985) and *Japan J. Breed.* 36, 1 (1986)]; Ling, D. H. et al., *Plant Cell Reports* 2, 169 (1983)). In these reports, the respective substances were said to promote a maximum redifferentiation efficiency of 300 individuals/g callus by their independent use. In the report of Raghavaram, N. V. and M. W. Nabors (*Plant Cell Tiss. Organ Cult.* 4, 241 (1985)), a redifferentiation ratio near 300 individuals/g callus was obtained by using a scutellum-derived callus. However, these reports were made relating to particular cultivars such as *Chyokoto, Pokkali, Taipei* 309, etc. and the application of their techniques to ordinary cultivars did not produce such redifferentiation ratios.

SUMMARY OF THE INVENTION

As discussed above, there are a number of reports on techniques for producing and inducing rice callus. However, there is no known case in which an E callus was induced efficiently and then proliferated efficiently while maintaining its embryogenic potency for a long time. The present invention enables the induction and proliferation of E callus without being restricted to a particular variety of rice.

The E callus referred to in the present invention is a callus composed of cells with high cytoplasmic density and small diameter, and having a smooth surface which appears vivid white to milk white under reflected light.

In contrast, callus having no embryogenic potency (hereinafter referred to as "NE callus") is composed of cells having low cytoplasmic density and large diameter (hereinafter referred to as "NE cells") and has a distinctly uneven surface which appears pale yellow to transparent.

The induction and proliferation of E callus is accomplished by culturing a rice explant in a liquid medium containing at least inorganic salts, at least one carbon source, at least one auxin and an osmotic regulator. Using the present invention, E callus can be induced and proliferated efficiently. By placing rice callus induced and/or proliferated according to the present invention on a medium for inducing a somatic embryo, an excellent rice somatic embryo can be obtained; by transferring the somatic embryo to a germination medium, a whole rice plant can be produced. The present invention thus enables the clonal proliferation of rice by first producing a somatic embryo from E callus and then producing a seedling from the somatic embryo.

The present clonal proliferation method requires no seed farm and is not influenced by natural conditions, thereby enabling the industrial production of juvenile rice plantlets (i.e. seedlings).

Furthermore, the present invention is applicable not onoly to a true bred cultivar but also to non-true bred cultivars. Thus, the present invention enables one to propagate non-true bred lines which, e.g., result as progeny from a crossing of cultivars which could not have been made previously.

DETAILED DESCRIPTION OF THE INVENTION

Figure 1:
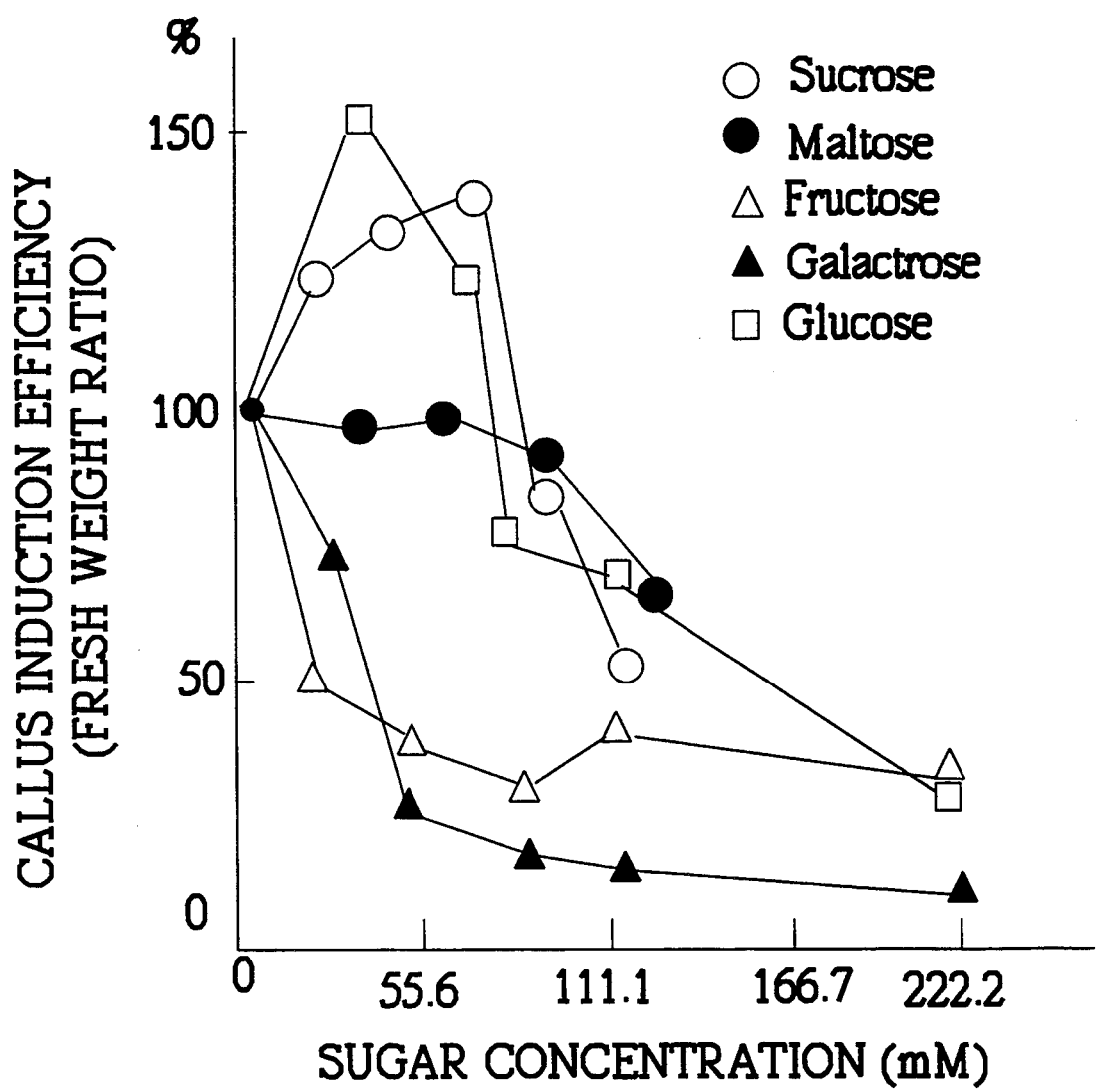
FIG. 1 is a graph showing the relationship between the sugar concentration of the medium and the callus induction efficiency.

Examples of rice explants that can be used with the present invention include: leaves (leaf blades and leaf sheaths), stems, seeds (brown rice), ovules, anthers, juvenile spikes, adventitious embryos, embryoids, and adventitious buds, etc. However, the present invention is in no way restricted to the explants mentioned on the foregoing list.

A medium for inducing an E callus from a rice explant (hereinafter referred to as an "induction medium") is one containing at least inorganic salts, a carbon source, one or more auxins and an osmotic regulator as essential components and, if desired, vitamins and amino acids. Such liquid media can be prepared by adding auxin and an osmotic regulator to conventional basal media which have been described for use in plant tissue culture, for example, N6 medium (Chu, C., C. Wang & C. Sun, *Scientica Sinica*, 18(5), 659 (1975)), Murashige-Skoog's medium (hereinafter referred to as "MS medium"), Linsmaier-Skoog's medium (hereinafter referred to as "LS medium"), White's medium, Gamborg's B-5 medium, Heller's medium, Kohlenbach-Schmidt's medium, and the like. The composition and preparation of these conventional media are described in Harada and Komanime, "Plant Cell Tissue Culture," pp. 390–391, Rikougakusha (1984).

As carbon sources for the medium, sucrose, glucose, and other simple sugars can be used, at concentrations preferably in the range of 5 to 40 g/l. As auxins, 2,4-D, naphthaleneacetic acid (NAA), and others can be used, either independently or in combination. Using 2,4-D, for example, it is preferable to add 0.5~10ppm. As osmotic regulators, mannitol, sorbitol, highly purified polyethyleneglycol (PEG), and others can be used. In the case of mannitol and sorbitol, it is preferable to use them in concentrations of 2 to 4% (w/v). In the case of PEG, the selected concentration will depend on its average molecular weight. Where the average molecular weight is around 1500, it is preferable to use concentrations below 3% (w/v).

In addition, it may be preferable to induce E callus by adding amino acids, a casein hydrolysate, etc., to the above induction medium, either independently or in combination. As amino acids, L-proline and others can be used. In the case of L-proline, it is preferable to use concentrations of 1 to 100 mM. Where a casein hydrolysate is included, it is preferably used in concentrations of 10 to 200 ppm. Furthermore, the addition of a cytokinin to the above induction medium may improve the callus induction ratio. As exemplary cytokinins, 4-PU (N-phenyl-N'-pyridyl urea) can be used. It is also preferable to adjust the pH of the medium to 5.5 to 6.0.

Specific culture conditions required for the induction of an E callus from an explant are as follows: Firstly, the aforementioned induction media are prepared, in which sterile or sterilized explants are inoculated. The sterilization of the explants can be carried out according to conventional techniques using, e.g., ethyl alcohol or a sodium hypochlorite solution. Then, the explants are cultured at 20 to 30° C. by shaking at 60 to 150 rpm, whereby E calli are obtained from the explants. In this method, light is not always essential. However, culture with a photoperiod of approximately 500~10,000 lux/8~16 hr. provides improved results.

According to the above method, suspensions containing E calli are obtained. The suspensions are filtered using 2 to 3 mm diameter meshes to remove the explants and then subjected to a conventional technique such as centrifugation or the like to harvest the E calli. The E calli so obtained are placed on induction medium and cultured under the same conditions as described for the induction process, whereby E calli are proliferated. Amino acids, a casein hydrolysate, cytokinin, etc., which give good results when added to the induction medium at the time of inducing E calli, show similar effects in the proliferation of E calli.

In practicing the above induction method, occasionally NE cells can be released from the explants. In this case, E calli can be separated out by utilizing the difference in density between the E callus and the NE cell. This separation is carried out, e.g., by conventional density gradient centrifugation using 16 to 20% ficoll or percoll or a 20 to 40% sucrose solution. After centrifugation, the supernatants are discarded, and precipitated E calli having high cytoplastic density are cultured in the same manner as described above, whereby E calli alone can be proliferated.

From the suspension of E callus obtained as described above, E calli are harvested by filtration, centrifugation, decantation, etc. The harvested E calli are washed with media containing no hormones (e.g., a hormone-free MS medium, etc.). The washed E calli are then cultured in an embryo-induction medium, as set forth below, whereby somatic embryos are formed.

The somatic embryo-induction medium is a medium containing at least inorganic salts, a carbon source and one or more auxins and, if desired, vitamins and amino acids. For example, media prepared by including auxins in the aforementioned MS medium, LS medium, etc., can be used.

As carbon sources for the medium, sucrose, glucose, and other simple sugars can be used, with concentrations preferably in the range of 5 to 40 g/l. As auxins, 2,4-D, naphthaleneacetic acid (NAA), and others can be used. With 2,4-D, for example, the auxin concentration is preferably 0.1 to 0.5 ppm.

Furthermore, a casein hydrolysate, an osmotic regulator, etc., can be added to the above embryo-induction medium either independently or in combination. The addition of a casein hydrolysate in concentrations of 1,000 to 2,000 ppm improves the production of somatic embryos.

As osmotic regulators, mannitol, sorbitol, highly purified polyethyleneglycol (PEG), and others can be used. In the case of a liquid medium, the addition of an osmotic regulator is particularly desirable. Using mannitol or sorbitol, for example, it is preferable to add them in concentrations of 2 to 10% (w/v). In the case of PEG, although the concentration selected will depend on its molecular weight, it is preferable to use concentrations of 0.5 to 2% (w/v).

In the case of a solid medium, using agar, gellan gum, etc., it is also preferable to add an osmotic regulator. Although using these substances in concentrations as high as is normal, an effect nearly equal to that of adding an osmotic regulator can be obtained, the combinational use of both can give preferable results.

In some cases, good results can be obtained by adding a cytokinin and/or abscisic acid as alternative plant hormones to the auxins mentioned above. As a cytokinin, kinetin can be used, preferably in concentrations of 0.01 to 0.5 ppm. Regarding the addition of abscisic acid, particularly preferable results can be obtained using concentrations of 0.1 to 1.0 ppm, for example, in the case of shake cultures.

Specific culture conditions for producing a somatic embryo from an E callus are as follows: Firstly, embryo-induction medium, as described above, is prepared, the E calli are inoculated therein and then cultured at approximately 20° to 30° C., whereby somatic embryos are formed. When using liquid medium, it is preferable to culture the E calli by shaking at 60 to 150 rpm. In the somatic embryo-producing process, light is not always essential. However, culturing the E calli with a photoperiod of approximately 500~10,000 lux/8~16 hr. can provide improved results.

A somatic embryo obtained according to the above method is then transferred to a germination medium, described below, whereby a rice plant can be obtained.

However, in some situations it may be preferable to first culture the somatic embryo in an embryo-maturation medium, as set forth below, and then transferring the matured embryo to the germination medium.

The embryo-maturation medium is a medium containing at least inorganic salts, a carbon source and one or more auxins as essential components and, if desired, vitamins and amino acids. For example, media prepared by adding auxin to the aforementioned MS medium, N6 medium, etc., can be used.

As carbon sources of the medium, sucrose, glucose, and other simple sugars can be used, at concentrations preferably in the range of 5 to 40 g/l. As an auxin, 2,4-D, NAA, IBA, DICAMBA (4-amino-3,5,6-trichloropicolinic acid), and others can be used, independently or in combination. Good results can be obtained using auxin concentrations of 0.1 to 0.5 ppm, for example, in the case of 2,4-D.

Furthermore, good results can also be obtained by adding cytokinin, abscisic acid, an osmotic regulator, a casein hydrolysate, etc., to the above described embryo-maturation medium, either independently or in combination. As cytokinin, kinetin or the like can be used and, in the case of kinetin, concentrations of 0.01 to 0.5 ppm give good results. As osmotic regulators, those described above for the embryo-induction medium can be used. In the case of mannitol, the addition in concentrations of 4 to 8% gives good results. The addition of casein hydrolysate in concentrations of 0.1 to 0.2% (w/v) also gives good results. It is also preferable to adjust the medium pH to 5.5 to 6.0.

The embryo-maturing process is accomplished by transferring the somatic embryo obtained as described above to the embryo-maturation medium and then culturing it at approximately 20° to 30° C. for two to four weeks. Although light is not always essential, it is preferable to culture the somatic embryo with a photoperiod of approximately 500~10,000 lux/8~16 hr.

The embryo obtained as described above is then cultured in a germination medium, as set forth below, to produce rice plants.

The germination medium is a medium containing at least inorganic salts and a carbon source as essential components and, if desired, vitamins and amino acids. For example, the aforementioned MS medium, LS medium, etc. can be used. As carbon sources, those given in the description of the induction medium can be used similarly. Good results can be obtained by adding auxin, cytokinin, casein hydrolysate, etc., to the above germination medium, either independently or in combination. Particularly, the addition of one or more auxins gives good results. As auxins, those mentioned in the description of the embryo-induction medium can be used and, in the case of 2,4-D, it is particularly preferable to add concentrations of 0.01 to 0.09 ppm. As cytokinins, kinetin and the like can be used, and, in the case of kinetin, concentrations of 0.01 ppm or greater are preferable. Furthermore, the addition of a casein hydrolysate in concentrations of 1,000 to 2,0000 ppm gives particularly good results.

By placing a somatic embryo on the above germination medium and then culturing without shaking at 20° to 30° C. with a photoperiod of approximately 500~10,000 lux/8~16 hr., a rice plant can be produced.

EXAMPLE 1

Full-ripe seeds of *Oryza sativa* L. cultivars Akenohoshi and Hoshinokikari were husked and surface-sterilized with a 70% ethanol solution and a sodium hypochlorite solution, washed with sterile water and then sown on sterile filter papers or 0.8% agar media. The husked seeds were then cultured at 25° C. in the dark for three to five days. Thereafter, foliage parts were excised from germinated seedlings and cut into 1 mm wide strips for use as explants.

Approximately 10 g of each explant was inoculated into an induction medium (N6 liquid medium containing 12 mM proline, 100 ppm casein hydrolysate, 3% mannitol, 2% sucrose and 2 ppm 2,4-D) and cultured by shaking at 90 rpm with a photoperiod of approximately 500 lux/12 hr.

As a result, callus formation began after approximately two weeks, and suspensions of E callus were formed after approximately eight weeks. The suspensions were then filtered using 1 mm diameter mesh screens to remove explants and then subcultured to proliferate in the above induction medium.

After the passage of several generations, the resulting suspensions were washed with hormone-free medium, resuspended in embryo-induction medium (MS medium containing 3% mannitol, 2,000 ppm casein hydrolysate, either 0.1 or 0.5 ppm 2,4-D, either 0.01, 0.05 or 0.5 ppm kinetin and 1% sucrose) and then cultured by shaking at 90 rpm with a photoperiod of approximately 500 lux/12 hr.

As a result, somatic embryos appeared after approximately six weeks and the formation of embryos was observed continuously for the following four weeks. The somatic embryos thus obtained were cultured without shaking on germination medium (MS medium containing 2% sucrose, 2,000 ppm casein hydrolysate, 0.05 ppm kinetin and 0.05 ppm 2,4-D) at 25° C. with a photoperiod of 4,000 lux/12 hr., whereby juvenile plantlets each having a length of a little less than 10 mm were obtained.

Somatic embryos having a diameter of 1 mm or less were cultured on embryo-maturation medium (MS medium containing 2,000 ppm casein hydrolysate, 3% sucrose, 0.5 ppm kinetin, 1 ppm 2,4-D, 2.2 mM DICAMBA and 5.4% sorbitol) for two to four weeks and then placed on germination medium (MS medium containing 2% sucrose, 2,000 ppm casein hydrolysate, 0.05 ppm kinetin and 0.05 ppm 2,4-D), whereby a large number of juvenile plantlets were obtained.

EXAMPLE 2

Full-ripe seeds of *Oryza sativa* L. cultivars Norin No. 21, Nihonbare, Yamabiko, Yashuuhatamochi, IR-26 and Chyokoto, which had been surface-sterilized in the same manner as described in Example 1 were inoculated directly into liquid induction medium (MS medium containing 3% mannitol, 4 ppm 2,4-D, 100 ppm casein hydrolysate and 2% sucrose) at the concentration of 1 seed grain/ml medium, and then cultured under the same conditions as described in Example 1.

For all cultivars, callus initiation occurred mainly from the root primordium part of the brown rice seed after approximately two weeks and suspensions were formed after eight weeks. After filtering out explants with 1 mm diameter mesh screens, the resulting suspensions were subcultured.

These suspensions were composed of E calli having high cytoplasmic density, NE callus cells having large diameter and low cytoplasmic density (which were released from the explants), and NE cell clusters. In order to separate out the E calli, the suspensions were fractionated by density gradient centrifugation using 16 to 20% ficoll or percoll or a 20 to 40% sucrose solution. The E calli obtained were washed with fresh induction medium and the subcultured in medium of the same composition.

The established suspensions of cultivars Norin No. 21, Nihonbare and Yamabiko were washed with hormone-free MS medium, resuspended in the embryo-induction medium described in Example 1, and then cultured by shaking under the same conditions. As a result, somatic embryos appeared after approximately six weeks, and the formation of embryos was observed continuously for four weeks thereafter. The somatic embryos obtained were cultured on germination media in the same manner as in Example 1, whereby juvenile plantlets each having a ground part with a length of a little less than 10 mm were obtained after approximately four weeks.

EXAMPLE 3

The culture was carried out in the same manner as described in Example 2 except that full-ripe seeds of cultivar Sasanishiki, surface-sterilized in the same manner as described in Example 1, were used and sucrose, maltose, glucose and fructose in various concentrations were independently used for carbon sources.

The fresh weight of callus obtained after four weeks from the beginning of culture was measured. The callus induction efficiency of each experimental plot was as given in FIG. 1, where the fresh weight of callus obtained from a culture with no added sugar was regarded as 100%.

When using brown rice for explants, E calli alone were induced on or before the third week of culture, even when no carbon source was included in the induction medium. Thereafter, the induced E calli were isolated from the explants and transferred to induction medium containing a carbon source as described in Example 1, whereby suspensions each containing E callus alone could be established.

It is believed that this result occurs because brown rice contains a carbon source, and thus a suspension of E callus is inducible without adding a carbon source to an induction medium. However, when the culture was continued without carrying out subculture, NE calli gradually appeared during or after the third week of culture, so that suspensions of E callus alone were not established. Where a carbon source was added, suspensions of E callus were established after the fourth week for all sugars and concentrations. However, the callus induction efficiency was particularly high in a plot where either 59 mM sucrose or 29 mM glucose was added.

EXAMPLE 4

Rice calli were induced in the same manner as described in Example 3 except that sugars were used in combination by fixing the total amount to be contained in the induction media to 117 mM (corresponding to 4% w/w for sucrose). As a result, E calli alone were induced in every plot.

Figure 2:
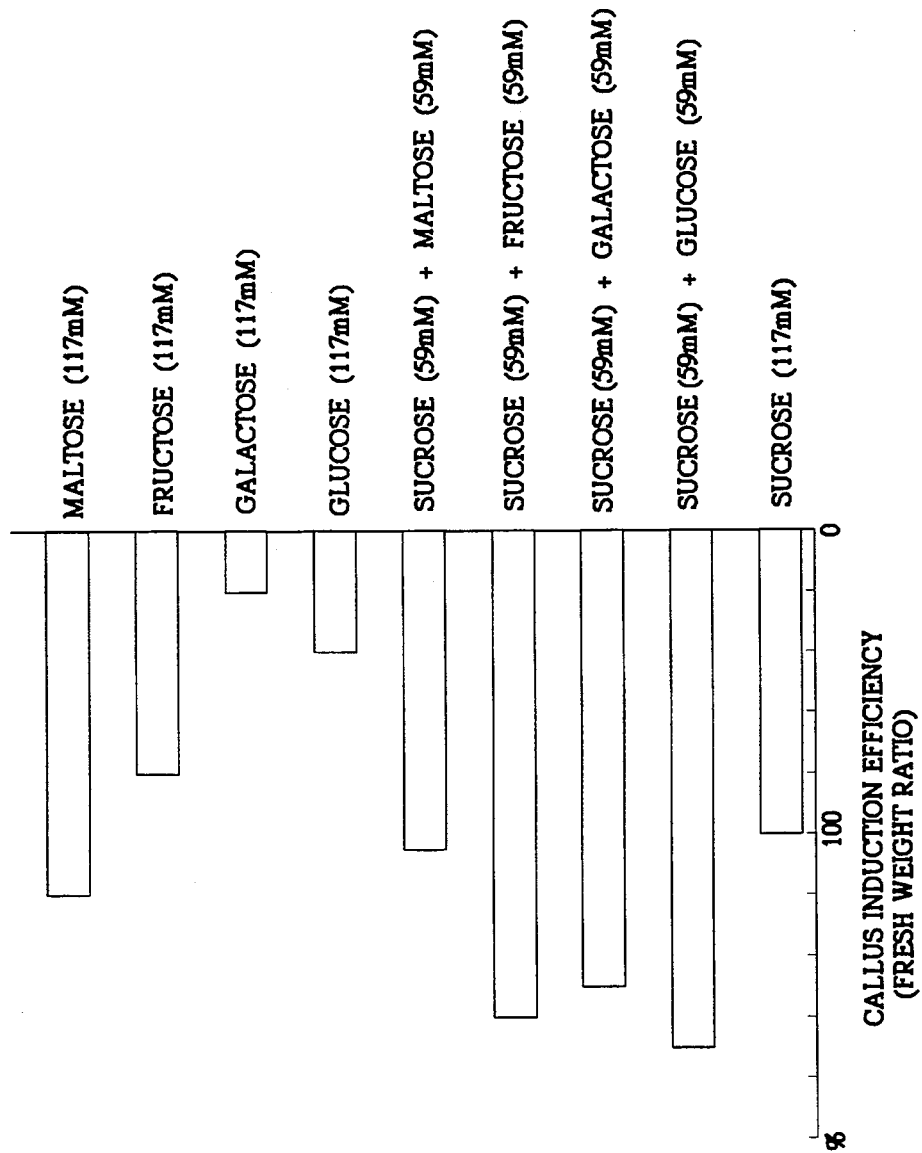
FIG. 2 is a graph showing the relationship between the variety of sugar added to the medium and the callus induction efficiency.

The fresh weight of calli obtained from each culture after four weeks from the beginning of culture was measured. The callus induction efficiencies obtained are shown in FIG. 2, wherein the plot where sucrose alone was used is taken as 100%. As a result, it was found that combining distinct carbon sources, such as glucose and the like with sucrose, was effective for the induction of E callus.

EXAMPLE 5

Suspension cultures of *Oryza sativa* L. cultivar Sasanishiki established as described in Example 3 were proliferated by culturing in the induction media described in Example 2 while varying the 2,4-D concentration of the media. The callus proliferation ratios after two weeks from the beginning of culture were examined.

Figure 3:
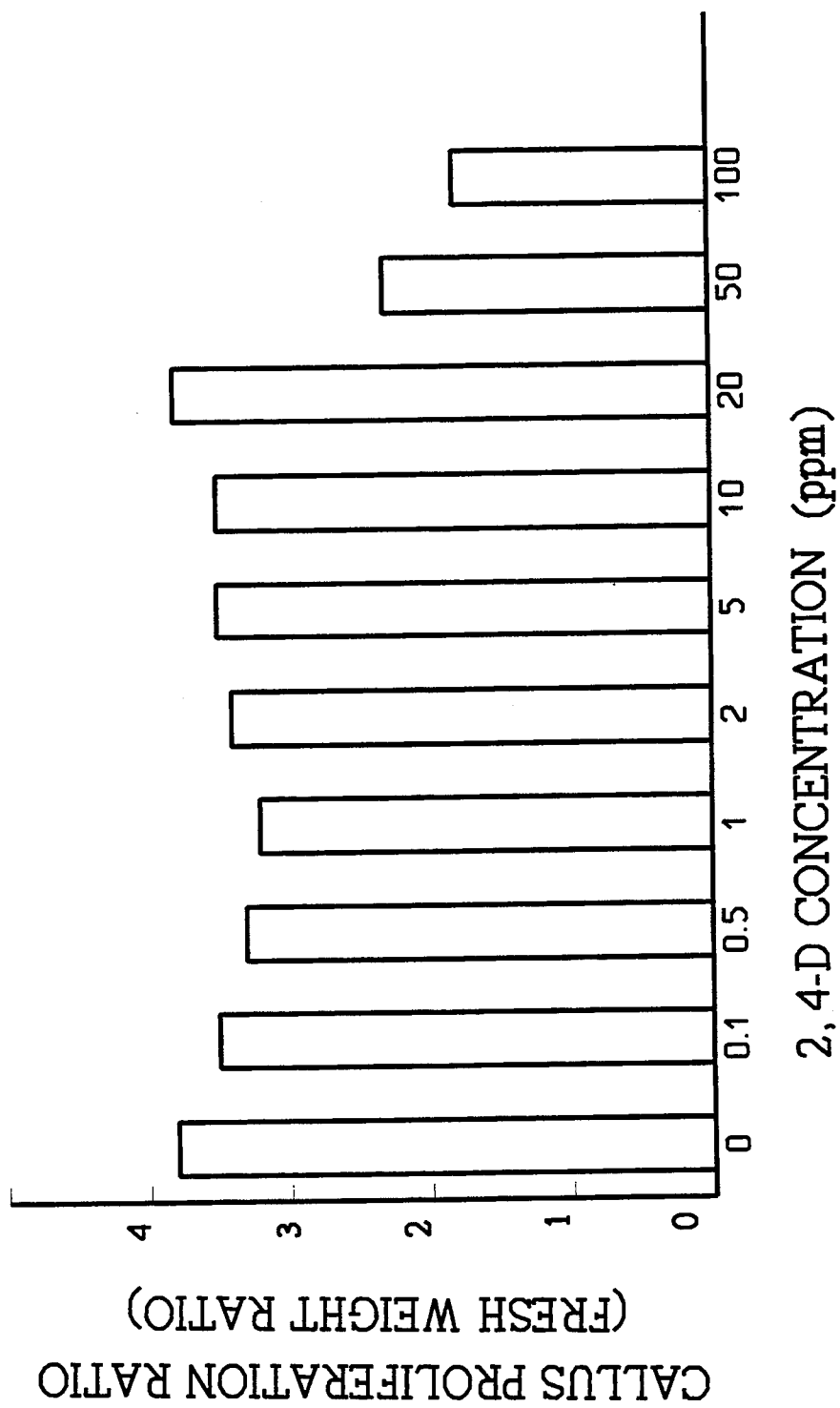
FIG. 3 is a graph showing the relationship between the 2,4-D concentration of the medium and the callus proliferation ratio.

The results are shown in FIG. 3, wherein the fresh weight of the callus at the time the culture was started is taken as 1. In all the plots, calli were proliferated. However, the calli were discolored in plots where 2,4-D had been added in concentrations of 0, 0.1 and 100 ppm respectively. On the other hand, vivid yellow E calli were obtained in plots where 0.5 to 50 ppm 2,4-D had been added.

EXAMPLE 6

Calli were cultured in the same manner as described in Example 2, except that suspensions of E callus of cultivar Sasanishiki obtained as described in Example 3 were used as specimens and sodium chloride or 4-PU (N-phenyl-N'-pyridyl urea) was added to the induction media. Two weeks after the beginning of culture, calli were harvested and the callus proliferation efficiency of each plot was examined.

Figure 4:
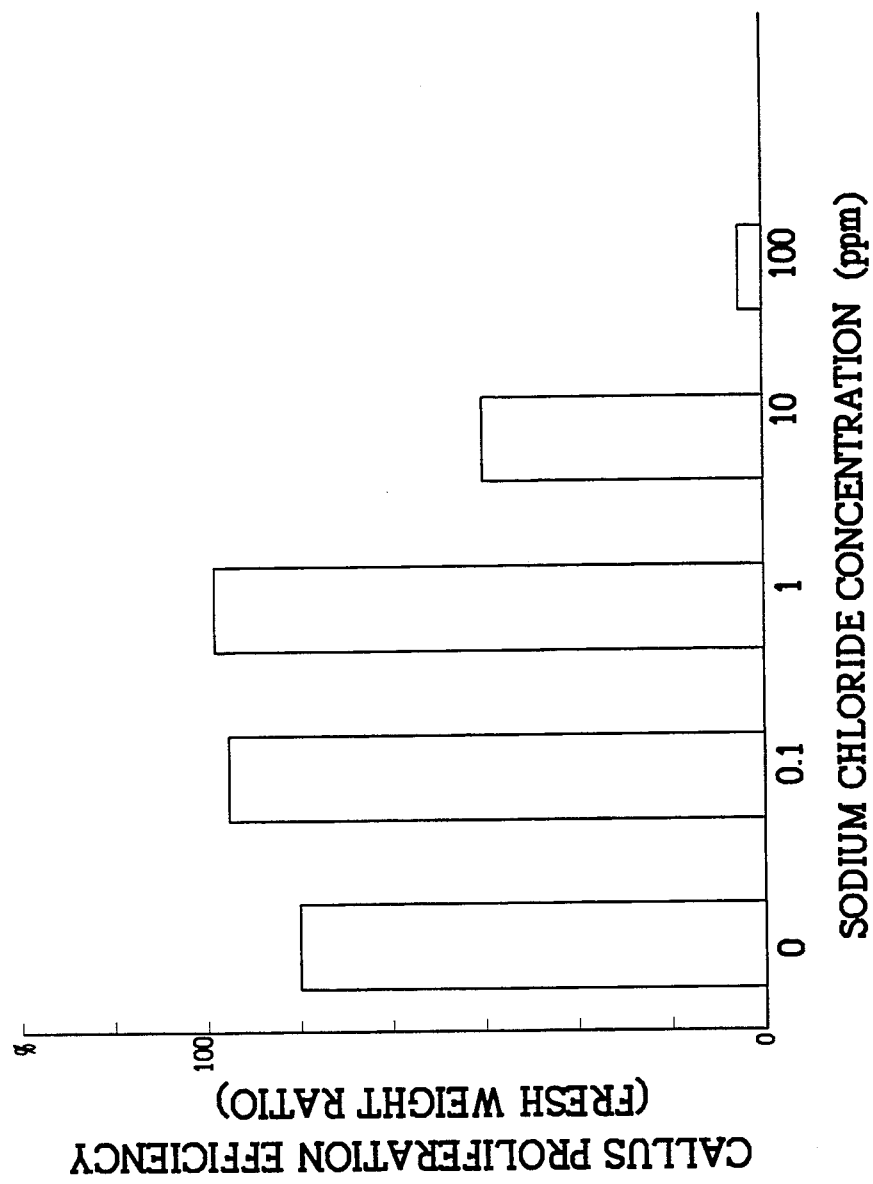
FIG. 4 is a graph showing the relationship between the sodium chloride concentration of the medium and the callus proliferation efficiency.
Figure 5:
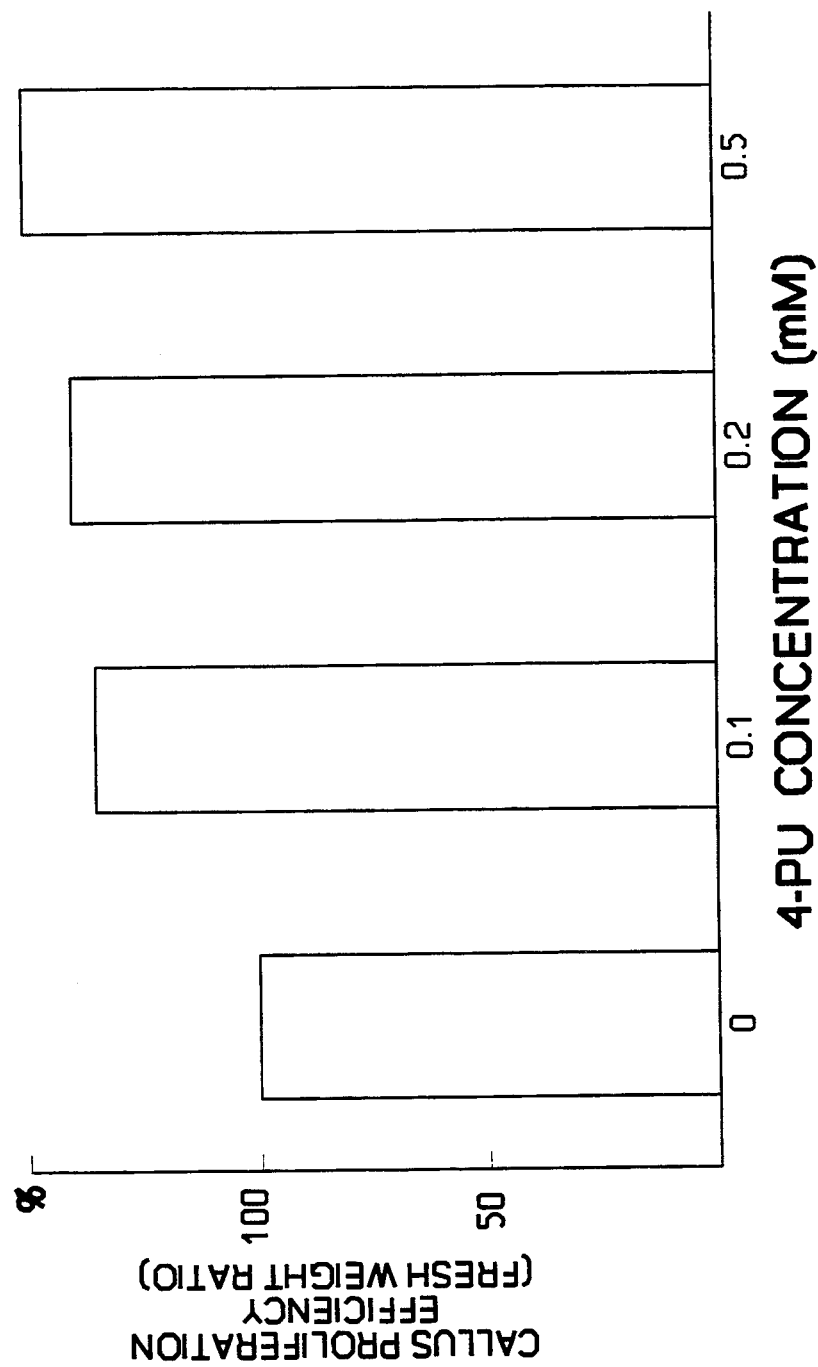
FIG. 5 is a graph showing the relationship between the 4-PU concentration of the medium and the callus proliferation efficiency.

The results were as shown in FIGS. 4 and 5, where the fresh weight of callus for each of the plots where neither sodium chloride nor 4-PU had been added was regarded as 100%. As shown, the proliferation efficiency was improved by the addition of 0.1 or 1 ppm sodium chloride or 0.1 to 0.5 ppm 4-PU.

EXAMPLE 7

Suspensions of cultivar Hoshinohikari were established as described in Example 2 and cultured to proliferate in the induction media described in Example 2 together with varying concentrations of mannitol and sucrose. After three weeks from the beginning of culture, the fresh weight of each callus was measured.

Figure 6:
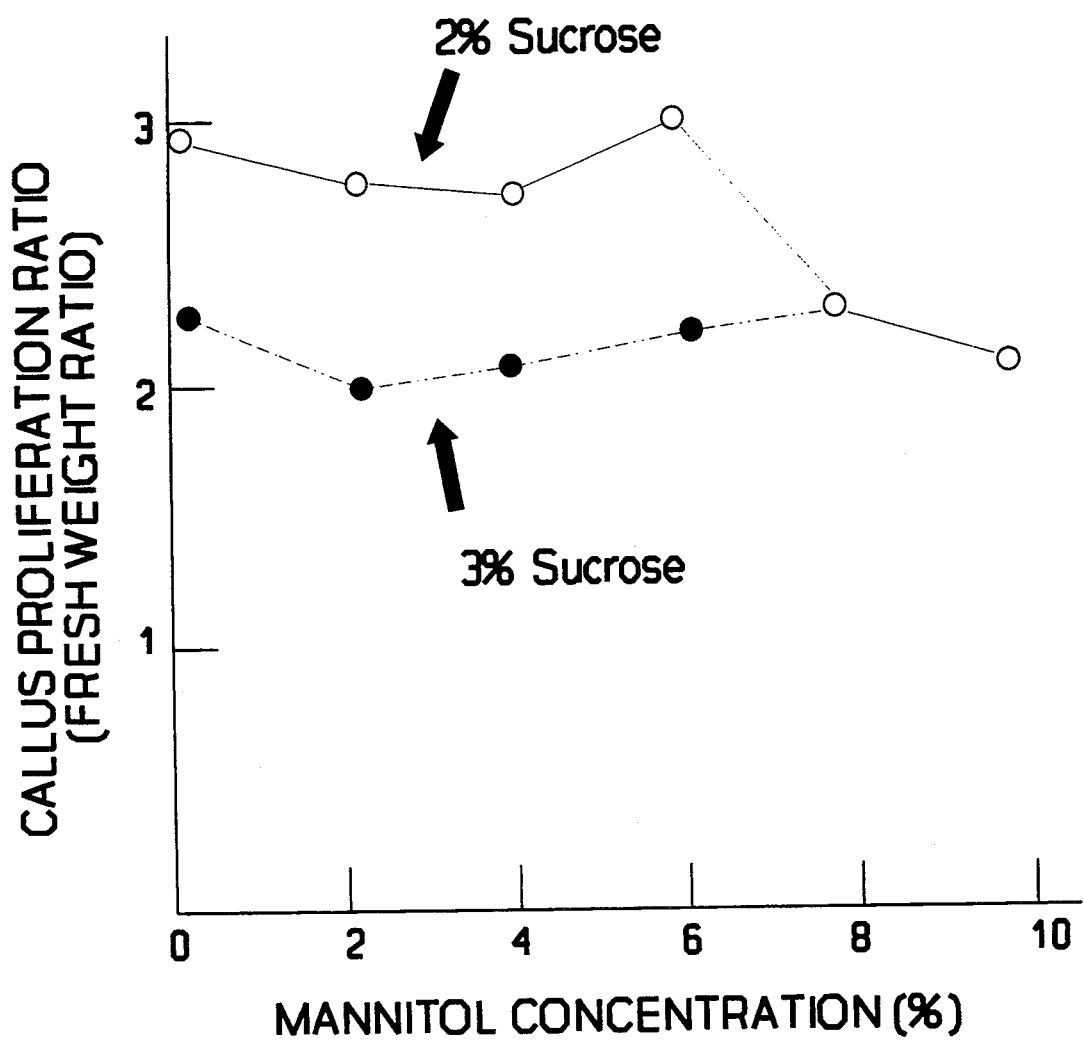
FIG. 6 is a graph showing the relationship between the mannitol concentration of the medium and the callus proliferation ratio, and, FIG. 7 is a graph showing the relationship between the DICAMBA concentration of the medium and the callus proliferation efficiency.

The proliferation efficiency was examined by obtaining the ratio of the fresh weight of callus measured above to that of the callus at the beginning of culture. The results were as shown in FIG. 6.

In suspension cultures of E callus established in mannitol-containing media which were transferred to mannitol-free media, although calli were proliferated, NE calli gradually appeared. In cultures where 2% or more of mannitol was added, E calli alone were proliferated. Within the concentration range of 10% or less, the difference in the mannitol concentration did not significantly influence the proliferation ratio. With respect to the sucrose concentration, the proliferation ratio in cultures having 3% always exceeded the ratio in cultures having 2%.

EXAMPLE 8

Full-ripe seeds of 3 cultivars of rice (Akenohoshi, Hatsuboshi and Hoshinokikari), were husked and surface-sterilized with a 70% ethanol solution and a sodium hypochlorite solution, then washed with sterile water and sown on sterile filter papers or on 0.8% agar media. The sown full-ripe seeds were cultured at 25° C. in the dark for three to five days.

Then, each developing zone having a length of approximately 15 mm from the tip of a root having a total length of approximately 20 mm or more was cut out for use as an explant. These explants were placed in embryoid-induction medium (N6 liquid medium containing 12 mM proline, 100 ppm casein hydrolysate, 3% mannitol, 2% sucrose and 2 ppm 2,4-D) at a concentration of 20 g/l medium, and cultured by shaking at 90 rpm with a photoperiod of approximately 500 lux/12 hr. After three days, embryoid formation began to be observed, and embryoids harvesting was begun for all cultivars.

Embryoids obtained after 12 weeks from the beginning of culture were inoculated as explants in the liquid medium described in Example 1 and cultured under the same conditions as described in Example 1.

For all cultivars, callus initiation took place after approximately two weeks and suspensions of E callus were formed after approximately eight weeks. The established suspensions were filtered using 1 mm diameter mesh screens to separate out explants, and then subcultured and allowed to proliferate in the same induction medium as described above.

After the passage of several generations, the resulting suspensions were washed with hormone-free medium, resuspended in embryo-induction medium as described in Example 1, and finally cultured by shaking at 90 rpm with a photoperiod of approximately 500 lux/12 hr., whereby somatic embryos were formed. After transferring the somatic embryos to germination medium as described in Example 1, rice plants were obtained.

EXAMPLE 9

Figure 7:
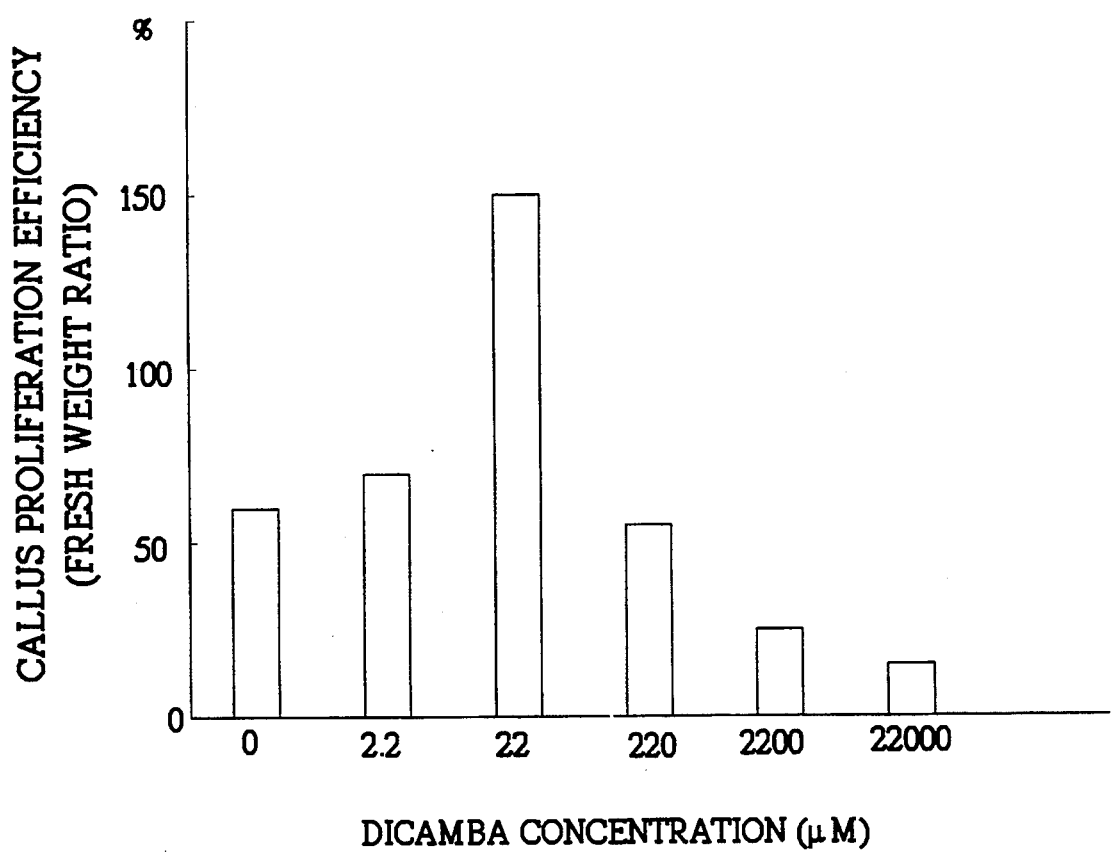

Suspensions of cultivar Sasanishiki obtained as described in Example 3 were cultured as described in Example 2 except that DICAMBA was used in place of 2,4-D. The growth increments of the callus observed after two weeks of culture were compared, where the 4 ppm 2,4-D-added plot was used as a control. The results are shown in FIG. 7. The addition of 22 $\mu$M DICAMBA brought about efficient proliferation of E callus as compared with that of 2,4-D.

EXAMPLE 10

Suspensions of cultivar Sasanishiki established as described in Example 3 were washed with hormone-free medium, placed in the embryo-induction medium described in Example 2, to which abscisic acid was added in various concentrations, and then cultured by shaking under the culture conditions as described in Example 2.

As a result, comparing the induction efficiencies of adventitious embryos after eight weeks from the beginning of culture, the plots where abscisic acid had been added in concentrations of 0.1 to 1.0 ppm showed particularly high induction efficiencies (see Table 1).

TABLE 1

| Basal Medium | Somatic Embryo Induction Ratios Abscisic Acid Concentration (ppm) | | | | | | | |
|---|---|---|---|---|---|---|---|---|
| | 0.01 | 0.05 | 0.1 | 0.5 | 1.0 | 5.0 | 10.0 | 50.0 |
| MS medium | + | + | ++ | +++ | ++ | + | + | − |

No induciton: −
Low induction ratio: + < ++ < +++: High induction ratio

We claim:

1. A method for producing a rice plant comprising:
   (a) inducing in a liquid medium rice callus having embryogenic potency comprising culturing husked seed of rice (*Oryza sativa* L.) in a liquid medium substantially free of solidifying agents, said medium containing:
   inorganic salts,
   at least one carbon source,
   at least one auxin, and
   at least one member selected from the group consisting of mannitol, sorbitol and polyethylene glycol;
   (b) proliferating said rice callus of step a) comprising culturing said callus in a liquid medium substantially free of solidifying agents, said medium containing:
   inorganic salts,
   at least one carbon source,
   at least one auxin, and
   at least one member selected from the group consisting of mannitol, sorbitol and polyethylene glycol;
   (c) culturing said callus of step b) in a liquid medium substantially free of solidifying agents, said medium containing:
   inorganic salts,
   at least one carbon source,
   at least one auxin,
   at least one osmotic regulator selected from the group consisting of mannitol, sorbitol and polyethylene glycol,
   at least one cytokinin, and
   at least one member selected from the group consisting of an amino acid and casein hydrolysate,
   the components of said medium provided in amounts sufficient to cause the production of a somatic embryo from said callus; and
   (d) culturing said somatic embryo on a semi-solid medium containing:
   inorganic salts,
   at least one carbon source,
   at least one auxin,
   at least one cytokinin,
   at least one member selected from the group consisting of an amino acid and casein hydrolysate, and
   at least one solidifying agent selected from the group consisting of agar and gelrite,
   the components of said medium provided in amounts sufficient to convert said somatic embryo into a rice plant.

2. The method for producing a rice plant according to claim 1, wherein:
   the carbon source of steps c) and d) are independently selected from the group consisting of sucrose and glucose, and
   the auxin of steps c) and d) are independently selected from the group consisting of 2,4-D, NAA, IBA, IAA, DICAMBA and Picloram.

3. A method for producing a rice plant comprising:
   (a) inducing in a liquid medium rice callus having embryogenic potency comprising culturing husked seed of rice (Oryza sativa L.) in a liquid medium substantially free of solidifying agents, said medium containing:
   inorganic salts,
   at least one carbon source,
   at least one auxin, and
   at least one member selected from the group consisting of mannitol, sorbitol and polyethylene glycol;
   (b) proliferating said rice callus of step a) comprising culturing said callus in a liquid medium substantially free of solidifying agents, said medium containing:
   inorganic salts,
   at least one carbon source,
   at least one auxin, and
   at least one member selected from the group consisting of mannitol, sorbitol and polyethylene glycol;
   (c) culturing said callus of step b) in a liquid medium substantially free of solidifying agents, said medium containing:
   inorganic salts,
   at least one carbon source,
   at least one auxin,
   at least one osmotic regulator selected from the group consisting of mannitol, sorbitol and polyethylene glycol,
   at least one cytokinin, abscisic acid, and
   at least one member selected from the group consisting of an amino acid and casein hydrolysate,
   the components of the said medium provided in amounts sufficient to cause the production of a somatic embryo from said callus;
   (d) culturing said somatic embryo of step c) in a liquid medium substantially free of solidifying agents, said medium containing:
   inorganic salts,
   at least one carbon source,
   at least one auxin,
   at least one osmotic regulator selected from the group consisting of mannitol, sorbitol and polyethylene glycol,
   at least one cytokinin,
   at least one member selected from the group consisting of an amino acid and casein hydrolysate,
   the components of said medium provided in amounts sufficient to raise the potency of germination for said somatic embryo; and
   (e) culturing said somatic embryo obtained in (d) on a semi-solid medium containing:
   inorganic salts,
   at least one carbon source,
   at least one auxin,
   at least one cytokinin,
   at least one member selected from the group consisting of an amino acid and casein hydrolysate, and
   at least one solidifying agent selected from the group consisting of agar and gelrite,
   the components of said medium provided in amounts sufficient to convert the somatic embryo obtained in (d) into a rice plant.

4. The method for producing a rice plant according to claim 3, wherein:
   the carbon source of steps c), d) and e) are independently selected from the group consisting of sucrose and glucose, and
   the auxin of steps c), d) and e) are independently selected from the group consisting of 2,4-D, NAA, IBA, IAA, DICAMBA and Picloram.

* * * * *